United States Patent
Lorant et al.

(10) Patent No.: US 6,846,479 B2
(45) Date of Patent: Jan. 25, 2005

(54) SUNSCREEN COMPOSITIONS COMPRISING MINERAL OXIDES HAVING HYDROPHOBIC COATINGS AND GLYCOSIDE-SUBSTITUTED POLYDIMETHYLSILOXANES

(75) Inventors: Raluca Lorant, Thiais (FR); Paula Lennon, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/448,345

(22) Filed: May 30, 2003

(65) Prior Publication Data

US 2004/0076592 A1 Apr. 22, 2004

Related U.S. Application Data

(63) Continuation of application No. PCT/FR01/03603, filed on Nov. 16, 2001.

(30) Foreign Application Priority Data

Nov. 30, 2000 (FR) .............................................. 00 15517

(51) Int. Cl.$^7$ ............................. A61K 7/42; A61K 7/44; A61K 7/00
(52) U.S. Cl. .......................... 424/59; 424/60; 424/400; 424/401
(58) Field of Search ............................ 424/59, 60, 400, 424/401

(56) References Cited

U.S. PATENT DOCUMENTS 5,744,126 A * 4/1998 Horino et al. ................. 424/59
6,066,326 A * 5/2000 Afriat et al. ................. 424/401

FOREIGN PATENT DOCUMENTS

EP      0882673      * 12/1998
WO   WO9725971 A   *  7/1997

* cited by examiner

Primary Examiner—Shelley A. Dodson
(74) Attorney, Agent, or Firm—Burns, Doane, Swecker & Mathis, L.L.P.

(57) ABSTRACT

Stable, topically applicable cosmetic/dermatological compositions, notably W/O emulsions, well suited for the UV-photoprotection of the skin, lips and/or the hair, and/or for the makeup of the skin and/or the lips, contain a thus effective amount of at least one mineral oxide having a hydrophobic coating thereon, e.g., coated particulates of an oxide of titanium and/or zinc, and, as a stabilizing agent therefor, a thus effective amount of at least one oxyalkylenated polydimethylsiloxane bearing at least one glycoside residue substituent, formulated into a physiologically acceptable medium therefor.

25 Claims, No Drawings

SUNSCREEN COMPOSITIONS COMPRISING MINERAL OXIDES HAVING HYDROPHOBIC COATINGS AND GLYCOSIDE-SUBSTITUTED POLYDIMETHYLSILOXANES

CROSS-REFERENCE TO PRIORITY/PCT APPLICATIONS

This application claims priority under 35 U.S.C. § 119 of FR-00/15517, filed Nov. 30, 2000, and is a continuation of PCT/FR01/03603, filed Nov. 16, 2001 and designating the United States (published in the French language on Jun. 6, 2002 as WO 02/43690 A1; the title and abstract were also published in English), both hereby expressly incorporated by reference.

BACKGROUND OF THE INVENTION

1. Technical Field of the Invention

The present invention relates to a composition comprising a coated mineral oxide and a polydimethylsiloxane containing glycoside groups, especially in the form of a water-in-oil emulsion, and to the use of the said composition, especially in cosmetics, in particular for antisun care and/or protection of the skin, the lips and the hair.

2. Description of Related/Prior Art

It is common practice in the cosmetics field to use chemical screening agents to obtain antisun products. These chemical screening agents may be introduced fairly readily into emulsions by dispersion in the oily or aqueous phase of the emulsion, depending on their lipophilic or hydrophilic nature.

To obtain high protection factors, it is necessary to increase the content of chemical screening agents. However, for reasons of tolerance, it is sought to avoid using an excessively high level of chemical screening agents, and it is preferred to introduce, alongside or in place of the chemical screening agents, mineral physical blocking agents, in particular metal oxides such as, for example, titanium dioxide and zinc oxide, which offer excellent anti-UV properties and very good skin tolerability.

However, introducing these metal oxides poses problems of cosmetic acceptability. Specifically, the antisun products containing them are often in the form of relatively thick emulsions, which are difficult to apply and to spread, heavy and sticky. In addition, with certain mineral blocking agents, for instance titanium dioxide, these defects are accompanied by a whitening effect during spreading on the skin.

Moreover, it is sought to obtain antisun emulsions that have a fluid texture, since the fluid texture makes them more practicable, easier to apply and more pleasant to use. However, fluid emulsions are also more difficult to produce with mineral blocking agents, since metal oxides have the drawback of destabilizing the emulsions into which it is desired to introduce them, and especially when they are very fluid emulsions. This difficulty of introducing metal oxides is even greater when the oxide content exceeds 1% in the final composition.

The instability phenomena are reflected in particular by the aggregation of the solid particles, the creaming and sedimentation of the emulsions, a heterogeneous appearance of the emulsions, and a change in the texture over time, this change being reflected by a thickening of the texture, which also becomes granular and heterogeneous.

SUMMARY OF THE INVENTION

The present invention features compositions comprising stable emulsions, even when they are very fluid, having high protection factors by virtue of the presence of mineral blocking agents, and also having appreciable cosmetic acceptability.

Thus, it has now surprisingly, and unexpectedly been found that compositions comprising particular silicone surfactants and metal oxides having hydrophobic coatings are well suited for providing water-in-oil emulsions having good cosmetic properties (light, fresh and also rich feel) and good stability over time, even though the emulsion is very fluid and even though it contains a large proportion of metal oxides. Stable fluid emulsions are not obtained with standard silicone surfactants such as alkyldimethicone copolyols of the type such as Abil EM90.

Thus, the present invention features compositions containing, in a physiologically acceptable medium, at least one metal oxide having a hydrophobic coating and at least one oxyalkylenated polydimethylsiloxane containing at least one glycoside residue.

This invention also features the use of at least one oxyalkylenated polydimethyl-siloxane containing at least one glycoside residue to stabilize a composition containing at least one metal oxide with a hydrophobic coating.

In the present patent application, the expression "physiologically acceptable medium" means a medium that is compatible with the skin, including the scalp, mucous membranes and/or the eyes.

Moreover, the expression "hydrophobic coating" means herein a coating that has no affinity for water and that does not get wet with water. This coating is obtained by means of one or more surface treatments of the metal oxide with one or more hydrophobic compounds.

DETAILED DESCRIPTION OF BEST MODE AND SPECIFIC/PREFERRED EMBODIMENTS OF THE INVENTION

More particularly accordingly to the present invention, water-in-oil emulsions are advantageously provided, comprising, in a physiologically acceptable medium, at least one metal oxide having a hydrophobic coating, and at least one oxyalkylenated polydimethylsiloxane containing at least one glycoside residue.

The compositions obtained according to the invention, especially those in the form of emulsions, present the advantage of spreading easily and of being absorbed quickly and completely into the skin. Along with having a rich and nutritive feel, they provide a surprising sensation of freshness. After penetration of the product, the skin remains soft and matt.

Moreover, the compositions according to the invention may contain a large percentage of physical blocking agents and thus impart a high SPF (sun protection factor) while at the same time being entirely stable and pleasant to use.

The oxyalkylenated polydimethylsiloxane containing at least one glycoside residue are advantageously selected from among the compounds of formula (I):

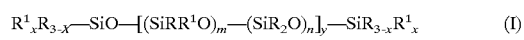

$$R^1{}_xR_{3-x}-SiO-[(SiRR^1O)_m-(SiR_2O)_n]_y-SiR_{3-x}R^1{}_x \quad (I)$$

in which:

m may be identical or different and is 0 or a number from 1 to 200, n may be identical or different and is 0 or a number from 1 to 1,000, x is 0 or 1, y is 0 or a number from 1 to 1,200, the radicals R may be identical or different and each represents a hydrogen atom or an optionally substituted hydrocarbon-based radical containing from 1 to 18 carbon atoms, the radicals $R^1$ may be identical or different and each represents a radical of formula (II):

$$Z—(R^2O—)_c—R^3 \quad \quad (II)$$

in which:

Z represents a glycoside residue derived from 1 to 10 monosaccharide or oligosaccharide units,
the radicals $R^2$ may be identical or different and each represents an alkylene radical,
c is 0 or a number from 1 to 20, and
$R^3$ represents an alkylene radical, with the proviso that the compound of formula (I) comprises at least one radical $R^1$.

In formula (II), Z is preferably a residue derived from monosaccharides. As monosaccharides from which Z may be derived, mention may be made especially of hexoses and pentoses, for instance glucose, fructose, galactose, mannose, talose, allose, altrose, arabinose, xylose, lyxose and ribose. Z is preferably a residue derived from glucose.

The compounds of formula (I) used in the composition of the invention may be prepared by any suitable process and especially according to the process disclosed in EP-A-612,769 which is incorporated herein by way of reference, by preparation of a glycoside obtained by reacting a monosaccharide or an oligosaccharide with a compound of formula (III):

$$HO—(R^2O—)_c—R^4 \quad \quad (III)$$

in which $R^4$ represents an alkylene radical, and reacting the glycoside obtained with a suitable organosilicon compound.

The oxyalkylenated polydimethylsiloxane containing at least one glycoside residue may be used in unmodified form or as a mixture with an oily medium, and especially in one or more silicone oils, more particularly one or more volatile silicone oils.

Compounds of formula (I) that may especially be used include a compound in which one of the radicals R represents an octyl group and $Z—(R^2O—)_c—R^3$ represents a group derived from glucose (Z=glucoside residue), in which $R^2O$ is $CH_2O$ and $R^3$ is a propyl group $(CH_2)_3$. This may be more particularly polydimethylsiloxane containing propyl-polyethoxyl diglucoside and octyl groups, as a dispersion containing 20% active material in cyclopentadimethylsiloxane (CTFA name: cyclopenta-siloxane/caprylyl-dimethicone ethoxyglucoside) sold under the name SPG 128 by the company Wacker.

The composition according to the invention may contain an amount of oxyalkylenated polydimethyl-siloxane containing a glycoside residue ranging from 0.1% to 20% by weight of active material and preferably from 0.5% to 10% by weight of active material relative to the total weight of the composition.

The metal oxides that may be used in the context of the present invention are any of those already known per se for their photoprotective activity. Thus, they may be chosen especially from titanium oxide (titanium dioxide in amorphous form or crystallized in rutile and/or anatase form), zinc oxide, iron oxide, zirconium oxide or cerium oxide, or mixtures thereof.

These metal oxides may be in the form of micrometer-sized particles or nanometer-sized particles (nanopigments). In the form of nanopigments, the mean particle sizes range, for example, from 5 to 100 nm. Nanopigments are preferably used in the composition of the invention.

The metal oxides with hydrophobic coating used according to the invention may have undergone, for example, one or more treatments with one or more compounds chosen from alumina, silica, aluminum derivatives (for example the stearate and laurate), silicon compounds (for example silicones, polydimethyl-siloxanes, alkoxysilanes or siloxysilicates), sodium compounds, iron oxides, iron esters (for example the stearate), fatty acids, fatty alcohols and derivatives thereof (such as stearic acid, hydroxystearic acid, stearyl alcohol, hydroxystearyl alcohol and lauryl alcohol, and derivatives thereof), lecithin, waxes (for example carnauba wax), (meth)acrylic polymers (for example polymethyl methacrylates) and fluoro compounds (for example perfluoroalkyl compounds and perfluoro-alkyl ethers). The oxides may also be treated with a mixture of these compounds or they may comprise several of these successive coatings.

The coated metal oxides used in the composition of the invention are preferably chosen from titanium oxides and zinc oxides, and mixtures thereof.

More particularly, the metal oxides with a hydrophobic coating used in the composition of the invention may be chosen from titanium oxides and nano-titanium oxides treated with:

alumina and stearic acid, for instance the product sold under the name UV-Titan M160 by Kemira, and the product sold under the name ST-430C by Inanata;
polydimethylsiloxanes (PDMS), for instance the products sold under the name Eusolex T-2000 by Merck, under the name UV Titan X170 by Eckart, or under the name Si-UFTR-Z by Myoshi;
alkoxysilanes, for instance the product sold under the name Covascreen T1 by Wackherr;
perfluoroalkyl compounds, for instance the product sold under the name PF-7 TiO2 MT-600B by Daito;
perfluoroalkyl ethers, for instance the product sold under the name TiO2 VF-25-3A by Toshiki;
siloxysilicates, for instance the product sold under the name TSS-1 by ISK;
polymethyl methacrylates, for instance the product sold under the name PW Covasil S by Wackherr;
lecithin, for instance the product sold under the name Duoterc CW 5-25 by Sachtleben;
carnauba wax, for instance the product sold under the name UVT-PT 951101 by Kemira;
silica and alumina, for instance the products sold under the names Microtitanium Dioxide MT 500 SA and Microtitanium Dioxide MT 100 SA by Tayca, and Tioveil Fin, Tioveil OP, Tioveil MOTG and Tioveil IPM by Uniquema;
alumina and aluminum stearate, for instance the product sold under the name Microtitanium Dioxide MT 100 T by Tayca;
alumina and aluminum laurate, for instance the product sold under the name Microtitanium Dioxide MT 100 S by Tayca;
iron oxides and iron stearate, for instance the product sold under the name Microtitanium Dioxide MT 100 F by Tayca;
silica, alumina and silicone, for instance the products sold under the names Microtitanium Dioxide MT 100 SAS, Microtitanium Dioxide MT 600 SAS and Microtitanium Dioxide MT 500 SAS by Tayca;
octyltrimethoxysilane, for instance the product sold under the name T-805 by Degussa;
alumina and glycerol, for instance the product sold under the name UVT-M212 by Kemira;
alumina and silicone, for instance the product sold under the name UVT-M262 by Kemira.

These hydrophobic coated titanium oxides and nanotitanium oxides may be in the form of a solid filler or in the form of a dispersion in an oily medium. Examples of dispersions of coated titanium oxide that may be mentioned include the products indicated above, sold by the company Uniquema under the names Tioveil FIN (nanotitanium oxide dispersed in C12–C15 alkyl benzoate, with a hydroxystearic acid polycondensate as dispersant) and Tioveil MOTG (nano-titanium oxide dispersed in mineral oil/triglycerides, with a hydroxystearic acid polycondensate as dispersant); the product sold under the name Covascreen TI by Wackherr (oily dispersion of TiO2 coated with trimethoxyoctylsilane at 60%); the product sold under the name Daitopersion TI-30 by Daito (dispersion of nanotitanium oxide coated with polymethylhydrogenosiloxane in cyclomethicone and dimethicone copolyol); the product sold under the name Tiosperse Ultra by Collaborative Laboratories (nanotitanium oxide coated with stearic acid/alumina, dispersed in 2-ethylhexyl hydroxystearate benzoate); the product sold under the name Mibrid Dispersion SAS4 5050 by Myoshi (nano-titanium oxide coated with alumina/stearic acid and then with polydimethylsiloxane, dispersed in cyclopentasiloxane); the product sold under the name SPD-T1 by Shin-Etsu (nanotitanium oxide coated with a silicone-grafted acrylic polymer and dispersed in cyclopentadimethylsiloxane).

According to one preferred embodiment of the invention, the following titanium oxides are used in the composition of the invention: SI-UFTR-Z, Tioveil MOTG, UV-Titan M160, Eusolex T-2000, PF-7 TI02 MT-600B, PW Covasil S, TSS-1, Covascreen TI, Daitopersion TI-30, Tiosperse Ultra, UV-Titan X 170, Mibrid Dispersion SAS4 5050, SPD-T1, Tioveil FIN, and more preferably the products UV-Titan X 170, Tiosperse Ultra, PW Covasil S, Mibrid Dispersion SAS4 5050 and SPD-T1.

As examples of zinc oxides that may be used in the composition of the invention, mention may be made of the nanozinc oxide dispersions sold under the names Daitopersion Zn-30 and Zn-50 by Daito, which are dispersions in cyclopolymethyl-siloxane/oxyethylenated polydimethylsiloxane, containing 30% or 50% of nanozinc oxides coated with polymethylhydrogenosiloxane.

One or more kinds of coated metal oxide may be used in the composition of the invention.

The amount of metal oxides in the composition of the invention may range, for example, from 0.5% to 30% by weight of active material, preferably from 2% to 20% by weight of active material and better still from 7% to 15% by weight of active material relative to the total weight of the composition.

The composition of the invention is intended for topical application and more particularly for application to the skin, the hair and/or mucous membranes. It may especially constitute a cosmetic and/or dermatological composition.

This composition may be in any pharmaceutical form normally used in cosmetics and dermatology, and it may especially be in the form of an optionally gelled oily solution, a dispersion of the lotion type optionally containing two phases, an emulsion obtained by dispersing a fatty (oily) phase in an aqueous phase (O/W) or, conversely, (W/O), or a multiple emulsion, for example a triple emulsion (W/O/W or O/W/O), or in the form of a vesicular dispersion of ionic type (liposomes) and/or nonionic type. These compositions are prepared according to the usual methods.

The composition of the invention may constitute, for example, a lotion, a milk or a cream that is relatively fluid. It may even be very fluid without being destabilized. The expression "very fluid" means herein a composition having a viscosity ranging from about 60 to 600 cPoises (60 to 600 mPa.s).

The composition according to the invention generally comprises an oily phase, which may consist of any fatty substance and especially any oil conventionally used in cosmetics. According to one preferred embodiment of the invention, the composition comprises at least one oil.

Among the oils that may be used in the composition of the invention, examples that may be mentioned include plant oils such as apricot kernel oil and soybean oil; mineral oils, for instance liquid petroleum jelly; synthetic oils, for instance isohexa-decane; volatile or non-volatile silicone oils and fluoro oils. Volatile silicone oils that may especially be mentioned include cyclic polydimethylsiloxanes or cyclomethicones which contain from about 3 to 9 silicon atoms and preferably from 4 to 6 silicon atoms, such as cyclohexadimethylsiloxane (or cyclohexamethicone) and cyclopentadimethylsiloxane (or cyclopentamethicone), and volatile linear polydimethylsiloxanes containing from about 3 to 9 silicon atoms. According to one preferred embodiment of the invention, the composition comprises at least one silicone oil.

The other fatty substances that may be present in the oily phase may be, for example, fatty acids, fatty alcohols and waxes such as petroleum jelly or beeswax.

When the composition is anhydrous, the amount of oily phase represents the difference to 100% by weight of the amounts of oxyalkylenated polydimethyl-siloxane containing at least one glycoside group and of metal oxide, i.e., the amount of oily phase may range, for example, from 50% to 99.4% by weight relative to the total weight of the composition.

According to one preferred embodiment of the invention, the composition is in the form of an emulsion and more especially in the form of a W/O emulsion, especially in the form of a fluid emulsion, i.e., an emulsion having a viscosity ranging from 60 to 600 cP (60 to 600 mPa.s) and better still from 80 to 250 cP (80 to 250 mPa.s), the viscosity being measured using a Metler RM 180 viscometer (Rheomat) with an M2 spindle, at 25° C. and at a speed of 200 rpm. A fairly fluid emulsion is thus obtained, which is very pleasant to use since it spreads easily and uniformly without leaving a greasy sensation or a coarse or sticky film.

The amount of oily phase in the emulsions and in particular in a W/O emulsion according to the invention may range, for example, from 5% to 80% and preferably from 40% to 70% by weight relative to the total weight of the emulsion. The aqueous phase of the emulsion may represent, for example, from 50% to 95% and preferably from 60% to 90% by weight relative to the total weight of the emulsion.

In a known manner, the composition of the invention may also contain adjuvants that are common in cosmetics, such as active agents, preserving agents, antioxidants, complexing agents, solvents, fragrances, fillers, sunscreens, bactericides, electrolytes (such as magnesium sulphate), odor absorbers, dyestuffs and lipid vesicles. The amounts of these various adjuvants are those that are conventionally used in the field under consideration, for example from 0.01% to 20% of the total weight of the composition. Depending on their nature, these adjuvants may be introduced into the oily phase, into the aqueous phase and/or into the lipid vesicles. These adjuvants and the concentrations thereof must be such that they do not modify the desired property for the composition of the invention.

According to one preferred embodiment of the invention, the composition comprises at least one sunscreen. As sunscreens, the composition of the invention may comprise any UVA and UVB screening agents that may be used in cosmetics.

Examples of UVB-screening agents that may be mentioned include:

(1) salicylic acid derivatives, in particular homo-menthyl salicylate and octyl salicylate;

(2) cinnamic acid derivatives, in particular 2-ethyl-hexyl p-methoxycinnamate, sold by Givaudan under the name Parsol MCX;

(3) liquid β,β'-diphenylacrylate derivatives, in particular 2-ethylhexyl α-cyano-α,β'-diphenylacrylate or octocrylene, sold by BASF under the name Uvinul N539;

(4) p-aminobenzoic acid derivatives;

(5) 4-methylbenzylidene camphor sold by Merck under the name Eusolex 6300;

(6) 2-phenylbenzimidazole-5-sulphonic acid sold under the name Eusolex 232 by Merck;

(7) 1,3,5-triazine derivatives, in particular:

2,4,6-tris[p-(2'-ethylhexyl-1'-oxycarbonyl)anilino]-1,3,5-triazine sold by BASF under the name Uvinul T150, and dioctylbutamidotriazone sold by Sigma 3V under the name Uvasorb HEB;

(8) mixtures of these screening agents.

Examples of UVA-screening agents that may be mentioned include:

(1) dibenzoylmethane derivatives, in particular 4-(tert-butyl)-4'-methoxydibenzoylmethane sold by company Givaudan under the name Parsol 1789;

(2) UVA-active screening agents of formula (IV) below:

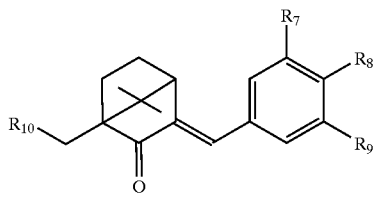

(IV)

in which:

$R_7$ and $R_9$, which may be identical or different, denote a hydrogen, a halogen, an OH radical, a saturated or unsaturated, linear or branched $C_1$–$C_{10}$ alkyl radical; a saturated or unsaturated, linear or branched $C_1$–$C_{1-0}$ alkoxy radical or an $HSO_3$ group;

$R_{10}$ denotes a hydrogen or $HSO_3$;

$R_8$ denotes an OH group; a group $OR_{11}$ in which $R_{11}$ denotes a saturated or unsaturated, linear or branched $C_1$–$C_{10}$ alkyl radical; or a group having the following structure:

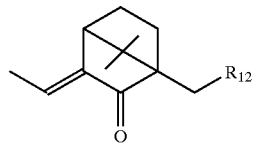

in which $R_{12}$ denotes hydrogen or $HSO_3$; or a group having the following structure:

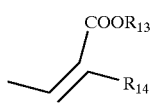

or alternatively a group having the following structure:

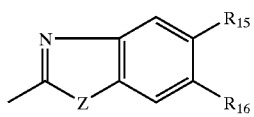

in which:

Z denotes an oxygen atom or an —NH— radical;

$R_{13}$, $R_{14}$, $R_{15}$ and $R_{16}$, which may be identical or different, denote a hydrogen, a halogen, an OH radical, a saturated or unsaturated, linear or branched $C_1$–$C_{10}$ alkyl radical; a saturated or unsaturated, linear or branched $C_1$-$C_{10}$ alkoxy radical or an $HSO_3$ group.

A compound of formula (IV) that may be mentioned in particular is benzene-1,4-bis(3-methylidenecamphor-10-sulphonic acid) optionally in partially or totally neutralized form, which corresponds to formula (V) below:

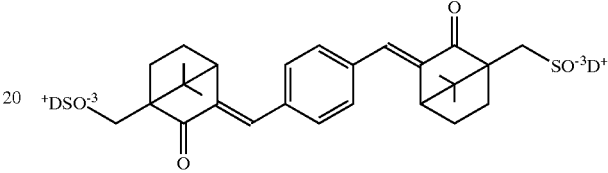

in which D denotes a hydrogen atom, an alkali metal or a radical $NH(R_{25})_3^+$ in which the radicals $R_{25}$, which may be identical or different, denote a hydrogen atom, a $C_1$–$C_4$ alkyl or hydroxyalkyl radical or a group $M^{n+}/n$, $M^{n+}$ denoting a polyvalent metal cation in which n is equal to 2 or 3 or 4, $M^{n+}$ preferably denoting a metal cation chosen from $Ca^{2+}$, $Zn^{2+}$, $Mg^{2+}$, $Ba^{2+}$, $Al^{3+}$ and $ZR^{4+}$, and in particular benzene-1,4-bis(3-methylidene-10-camphor-sulphonic acid), sold under the name Mexoryl SX by Chimex.

(3) benzophenone derivatives, for example:

2,4-dihydroxybenzophenone (benzophenone-1);
2,2',4,4'-tetrahydroxybenzophenone (benzophenone-2);
2-hydroxy-4-methoxybenzophenone (benzophenone-3), sold under the name Uvinul M40 by BASF;
2-hydroxy-4-methoxybenzophenone-5-sulphonic acid (benzophenone-4) and also its sulphonate form (benzophenone-5), sold by BASF under the name Uvinul MS40;
2,2'-dihydroxy-4,4'-dimethoxybenzophenone (benzophenone-6);
5-chloro-2-hydroxybenzophenone (benzophenone-7);
2,2'-dihydroxy-4-methoxybenzophenone (benzo-phenone-8);
the disodium salt of 2,2'-dihydroxy-4,4'-dimethoxy-benzophenone-5,5'-disulphonic acid (benzophenone-9);
2-hydroxy-4-methoxy-4'-methylbenzophenone (benzo-phenone-10);
benzophenone-11;
2-hydroxy-4-(octyloxy)benzophenone (benzophenone-12).

(4) silane derivatives or polyorganosiloxanes containing a benzophenone group;

(5) anthranilates, in particular menthyl anthranilate sold by Haarman & Reimer under the name Neo Heliopan MA;

(6) compounds comprising per molecule at least two benzazolyl groups or at least one benzodiazolyl group, in particular phenylene-1,4-bis(benzimidazolyl-3,3', 5,5'-tetrasulphonic acid) and also the salts thereof, of structure (VI) below:

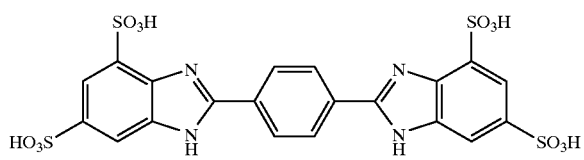

(VI)

sold by Haarman & Reimer;

(7) silicon derivatives of N-substituted benzimidazolyl-benzazoles or of benzofurylbenzazoles, and in particular:

2-[1-[3-[1,3,3,3-tetramethyl-1-[(trimethylsilyl)oxy]-disiloxanyl] propyl]-1H-benzimidazol-2-yl]benzoxazole;
2-[1-[3-[1,3,3,3-tetramethyl-1-[(trimethylsilyl)oxy]-disiloxanyl]propyl]-1H-benzimidazol-2-yl] benzothiazole;
2-[1-(3-trimethylsilanylpropyl)-1H-benzimidazol-2-yl] benzoxazole;
6-methoxy-1,1'-bis(3-trimethylsilanylpropyl)-1H,1'H-[2,2'] bibenzimidazolylbenzoxazole;
2-[1-(3-trimethylsilanylpropyl)-1H-benzimidazol-2-yl]-benzothiazole;
which are disclosed in EP-A-1,028,120;

(8) triazine derivatives, and in particular 2,4-bis{[4-(2-ethylhexyloxy)-2-hydroxy]phenyl}-6-(4-methoxyphenyl)-1,3,5-triazine sold by Ciba Geigy under the name Tinosorb S, and 2,2'-methylenebis[6-(2H-benzotriazol-2-yl)-4-(1,1,3,3-tetramethylbutyl)phenol] sold by Ciba Geigy under the name Tinosorb M;

(9) mixtures thereof.

A mixture of several of these screening agents and a mixture of UVB-screening agents and of UVA-screening agents may also be used.

The composition according to the invention is useful in numerous treatments, especially cosmetic treatments, of the skin, the lips and the hair, including the scalp, especially for protecting and/or caring for the skin, the lips and/or the hair and/or for making up the skin and/or the lips.

The composition according to the invention may be used, for example, as an antisun care and/or protection product for the face and/or the body in the form of creams or milks.

Thus, a subject of the invention is also the cosmetic use of the composition as defined above for the antisun care and/or protection of the skin, the lips and/or the hair, and/or for making up the skin and/or the lips.

A subject of the invention is also a cosmetic treatment process (regime or regimen) for protecting the skin, including the scalp, the hair and/or the lips against solar radiation, comprising topically applying onto the skin, the hair and/or the lips a composition as defined above.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLE 1

W/O Emulsion of SPF 40:

Oily Phase:

| | |
|---|---|
| PDMS containing polyethoxylated propyl diglucoside and octyl groups at 20% in cyclopentadimethylsiloxane (SPG 128 from Wacker) | 20% (i.e., 4% A.M.) |
| Cyclohexadimethylsiloxane | 20% |
| p-methoxycinnamate (Parsol MCX) (liposoluble screening agent) | 7% |
| PDMS-coated titanium dioxide (UV Titan X170 from Kemira) | 10% (A.M.) |

Aqueous Phase:

| | | |
|---|---|---|
| Glycerol | | 5% |
| Preserving agents | qs % | |
| Mexoryl SX (water-soluble screening agent) | | 3% |
| Demineralized water | qs | 100% |

Procedure:

Each of the two phases is homogenized and they are then mixed together with stirring, dispersing the aqueous phase in the oily phase.

A very soft fluid milk is obtained, which does not whiten on application. It has a fine, uniform appearance under a microscope and good dispersion of the pigments is observed.

This emulsion remains stable after storage for two months at 45° C.

COMPARATIVE EXAMPLE 1

W/O Emulsion with Uncoated Titanium Oxide:

Example 1 is repeated, but replacing the coated titanium oxide with the same amount of uncoated titanium oxide (Titanium Dioxide P25 sold by Degussa).

A coarse, unstable emulsion is obtained: coalescence of the drops of water and a release of water and oil take place a few hours after preparing the emulsion. Study of the emulsion by microscope confirms this instability.

COMPARATIVE EXAMPLE 2

W/O Emulsion with an Alkyl-dimethicone copolyol:

Example 1 is repeated, but replacing the PDMS containing polyethoxylated propyl diglucoside and octyl groups with the same amount of active material (4%) of an alkyldimethicone copolyol (cetyldimethicone copolyol: Abil EM90 from Goldschmidt).

An unstable emulsion is obtained: sedimentation of the droplets of aqueous phase and of the titanium dioxide, which are no longer uniformly distributed in the oily phase, takes place over time, and as a result oil also appears at the surface.

EXAMPLE 2

SPF 20 Fluid Foundation:

Oily Phase:

| | |
|---|---|
| PDMS containing polyethoxylated propyl diglucoside and octyl groups at 20% in cyclopentadimethylsiloxane (SPG 128 from Wacker) | 20% (i.e., 4% A.M.) |
| Cyclopentadimethylsiloxane | 30% |

-continued

| Brown, red and yellow pigments | 5% |
| Coated TiO$_2$ (Tiosperse Ultra) | 15% (A.M.) |

Aqueous Phase:

| Preserving agents | qs % | |
| Mexoryl SX (water-soluble screening agent) | | 3% |
| Water | qs | 100% |

Procedure:

The two phases are homogenized and the emulsion is then formed with stirring by dispersing the aqueous phase in the oily phase.

A very soft fluid foundation is obtained, which leaves the skin satiny. It has a fine, uniform appearance by microscope and good dispersion of the pigments is observed.

This emulsion remains stable after storage for two months at 45° C.

Each patent, patent application and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A stable cosmetic/dermatological composition suited for the UV-photoprotection of the skin, lips and/or the hair, and/or for the makeup of the skin and/or the lips, comprising a thus effective amount of at least one mineral oxide having a hydrophobic coating thereon and, as a stabilizing agent therefor, a thus effective amount of at least one oxyalkylenated polydimethylsiloxane bearing at least one glycoside residue substituent, formulated into a physiologically acceptable medium therefor.

2. A stable, topically applicable cosmetic/dermatological emulsion suited for the UV-photoprotection of the skin, lips and/or the hair, and/or for the makeup of the skin and/or the lips, comprising a thus effective amount of at least one mineral oxide having a hydrophobic coating thereon and, as a stabilizing agent therefor, a thus effective amount of at least one oxyalkylenated polydimethylsiloxane bearing at least one glycoside residue substituent, formulated into a physiologically acceptable medium therefor.

3. The stable cosmetic/dermatological composition as defined by claim 1, said at least one mineral oxide having a hydrophobic coating thereon comprising an oxide of titanium, zinc, iron, zirconium, cerium, or mixture thereof.

4. The stable cosmetic/dermatological composition as defined by claim 3, said at least one mineral oxide having a hydrophobic coating thereon comprising an oxide of titanium, zinc, or mixture thereof.

5. The stable cosmetic/dermatological composition as defined by claim 1, said at least one mineral oxide having a hydrophobic coating thereon comprising nanopigments thereof.

6. The stable cosmetic/dermatological composition as defined by claim 1, said at least one mineral oxide having a hydrophobic coating thereon having been treated with at least one of alumina, silica, an aluminum compound, a silicon compound, a sodium compound, an iron oxide, an iron ester, a fatty acid, a fatty alcohol or derivative thereof, lecithin, a wax, a (meth)acrylic polymer, a fluoro compound, or mixture thereof.

7. The stable, topically applicable cosmetic/dermatological emulsion as defined by claim 2, comprising a water-in-oil emulsion.

8. The stable cosmetic/dermatological composition as defined by claim 1, further comprising at least one oil.

9. The stable cosmetic/dermatological composition as defined by claim 1, further comprising at least one UV-A and/or UV-B sunscreen other than said at least one mineral oxide having a hydrophobic coating thereon.

10. The stable cosmetic/dermatological composition as defined by claim 1, said at least one oxyalkylenated polydimethylsiloxane bearing at least one glycoside residue substituent having the following structural formula (I):

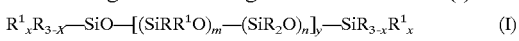

$$R^1_x R_{3-x}-SiO-[(SiRR^1O)_m-(SiR_2O)_n]_y-SiR_{3-x}R^1_x \quad (I)$$

in which the subscripts m, which may be identical or different, are each 0 or a number ranging from 1 to 200; the subscripts n, which may be identical or different, are each 0 or a number ranging from 1 to 1,000; the subscript x is 0 or 1; the subscript y is 0 or a number ranging from 1 to 1,200; the radicals R, which may be identical or different, are each a hydrogen atom or an optionally substituted hydrocarbon-based radical having from 1 to 18 carbon atoms; and the radicals R$^1$, which may be identical or different, are each a radical of formula (II):

$$Z-(R^2O-)_c-R^3 \quad (II)$$

in which Z is a glycoside residue derived from 1 to 10 monosaccharide or oligosaccharide structural units; the radicals R$^2$, which may be identical or different, are each an alkylene radical; the subscript c is 0 or a number ranging from 1 to 20; and R$^3$ is an alkylene radical, with the proviso that the compound of formula (I) comprises at least one radical R$^1$.

11. The stable cosmetic/dermatological composition as defined by claim 10, wherein formula (I), Z is derived from a hexose or a pentose.

12. The stable cosmetic/dermatological composition as defined by claim 10, wherein formula (I), Z is derived from glucose.

13. The stable cosmetic/dermatological composition as defined by claim 10, wherein formula (I), one radical R is an octyl radical and Z-(R$^2$O—)$_c$—R$^3$ is derived from glucose, with R$^2$O being CH$_2$O and R$^3$ a propyl radical.

14. The stable cosmetic/dermatological composition as defined by claim 1, said at least one oxyalkylenated polydimethylsiloxane bearing at least one glycoside residue substituent comprising admixture with at least one silicone oil.

15. The stable cosmetic/dermatological composition as defined by claim 1, said at least one oxyalkylenated polydimethylsiloxane bearing at least one glycoside residue substituent comprising from 0.1% to 20% by weight thereof.

16. The stable cosmetic/dermatological composition as defined by claim 1, said at least one oxyalkylenated polydimethylsiloxane bearing at least one glycoside residue substituent comprising from 0.5% to 10% by weight thereof.

17. The stable cosmetic/dermatological composition as defined by claim 1, said at least one mineral oxide having a hydrophobic coating thereon comprising from 0.5% to 30% by weight thereof.

18. The stable cosmetic/dermatological composition as defined by claim 1, said at least one mineral oxide having a hydrophobic coating thereon comprising from 2% to 20% by weight thereof.

19. The stable, topically applicable cosmetic/dermatological emulsion as defined by claim 2, the oily phase of which comprising from 5% to 80% by weight thereof.

20. The stable cosmetic/dermatological composition as defined by claim 1, formulated as an optionally gelled oily solution, a lotion, an ionic and/or nonionic vesicular dispersion, a milk, or a cream.

21. The stable cosmetic/dermatological composition as defined by claim 1, having a viscosity ranging from about 60 to 600 cPoises.

22. The stable cosmetic/dermatological composition as defined by claim 1, further comprising a conventional cosmetically/dermatologically active agent, a preservative, an antioxidant, a complexing agent, a solvent, a fragrance, a filler, a bactericide, an electrolyte, an odor absorber, a colorant, lipid vesicles, or mixture thereof.

23. A regime or regimen for the UV-photoprotection of the skin, lips and/or the hair, comprising topically applying thereon a thus effective amount of at least one mineral oxide having a hydrophobic coating thereon, and, as a stabilizing agent therefor, a thus effective amount of at least one oxyalkylenated polydimethylsiloxane bearing at least one glycoside residue substituent, formulated into a physiologically acceptable medium therefor.

24. A regime or regimen for the makeup of the skin and/or the lips, comprising topically applying thereon a thus effective amount of at least one mineral oxide having a hydrophobic coating thereon and, as a stabilizing agent therefor, a thus effective amount of at least one oxyalkylenated polydimethylsiloxane bearing at least one glycoside residue substituent, formulated into a physiologically acceptable medium therefor.

25. A regime or regimen for the UV-photoprotection of the skin, lips and/or the hair, comprising topically applying thereon a stable W/O emulsion which comprises a thus effective amount of at least one mineral oxide having a hydrophobic coating thereon and, as a stabilizing agent therefor, a thus effective amount of at least one oxyalkylenated polydimethylsiloxane bearing at least one glycoside residue substituent, formulated into a physiologically acceptable medium therefor.

* * * * *